(12) United States Patent
Ahrabi et al.

(10) Patent No.: US 8,912,162 B2
(45) Date of Patent: Dec. 16, 2014

(54) PARENTERAL FORMULATIONS OF ELACYTARABINE DERIVATIVES

(75) Inventors: Sayeh Ahrabi, Oslo (NO); Finn Myhren, Porsgrunn (NO); Ole Henrik Eriksen, Oslo (NO)

(73) Assignee: Clavis Pharma ASA, Oslo (NO)

( * ) Notice: Subject to any disclaimer, the term of this patent is extended or adjusted under 35 U.S.C. 154(b) by 0 days.

(21) Appl. No.: 13/809,653

(22) PCT Filed: Jul. 1, 2011

(86) PCT No.: PCT/NO2011/000189
§ 371 (c)(1),
(2), (4) Date: Mar. 19, 2013

(87) PCT Pub. No.: WO2012/008845
PCT Pub. Date: Jan. 19, 2012

(65) Prior Publication Data
US 2013/0196941 A1    Aug. 1, 2013

Related U.S. Application Data

(60) Provisional application No. 61/363,730, filed on Jul. 13, 2010.

(51) Int. Cl.
*A01N 43/04*     (2006.01)
*A61K 31/70*     (2006.01)
*A61K 9/00*      (2006.01)
*A61K 31/7056*   (2006.01)
*C07H 19/06*     (2006.01)
*A61K 9/127*     (2006.01)
*A61K 9/107*     (2006.01)

(52) U.S. Cl.
CPC ............. *C07H 19/06* (2013.01); *A61K 9/0019* (2013.01); *A61K 31/7056* (2013.01); *A61K 9/127* (2013.01); *A61K 9/1075* (2013.01)
USPC .............................................. 514/49; 514/43

(58) Field of Classification Search
None
See application file for complete search history.

(56) References Cited

FOREIGN PATENT DOCUMENTS

WO    9705154    2/1997

OTHER PUBLICATIONS

Rubas et al. Int. J. Cancer (1986), vol. 37, pp. 149-154.*
Mozafari Cellular & Molecular Biology Letters (2005), vol. 10, pp. 711-719.*
Werling et al. European Journal of Pharmaceutics and Biopharmaceutics (2008), vol. 69, pp. 1104-1113.*
Bergman et al. Nucleosides, Nucleotides and Nucleic Acids (2004), vol. 23, pp. 1523-1526.*
O'Brien et al. BCR-ABL, Alternative Splicing Profiles in, and Positive Acute Lymphoblastic. "A Phase II Multicentre Study With Elacytarabine in Late Stage Acute Myeloid Leukaemia." 15th Congress of the European Hematology Association Barcelona, Spain Jun. 10-13, 2010. vol. 93. No. s1. 2008.*
Schwendener, R.A., "Liposomes as carriers for lipophilic antitumor prodrugs. Incorporation characteristics and in vivo cytotoxic activity." Liposomes as drug carriers: 1986, pp. 170-181.
Schwendener, R.A., " Lipophilic 1-beta-D-arabinofuranosyl cytosine derivatives in liposomal formulations for oral and parenteral antileukemic therapy in the murine L1210 leukemia model." J. cancer Res. Clin. Oncol. (1996), 122: 723-726.
Dueland, S., "Intravenous administration of CP-4055 (ELACYT) in patients with solid tumours. A Phase I study." Acta Oncologica, 2009; 48: 137-145.

* cited by examiner

*Primary Examiner* — Patrick Lewis
(74) *Attorney, Agent, or Firm* — Fitzpatrick, Cella, Harper & Scinto

(57) ABSTRACT

The present invention relates to parenteral formulations for certain long chain saturated and monounsaturated fatty acid derivatives of 1-β-D-arabinofuranosylcytosine (cytarabine). In particular, the present invention relates to a parenteral pharmaceutical composition and a method of the preparation thereof, in order to accommodate therapeutically effective doses of the said derivatives ameliorating compliance in treatment of cancer.

18 Claims, 2 Drawing Sheets

PARENTERAL FORMULATIONS OF ELACYTARABINE DERIVATIVES

FIELD OF THE INVENTION

The present invention relates to a pharmaceutical composition comprising certain long chain saturated and monounsaturated fatty acid derivatives of 1-β-D-arabinofuranosylcytosine (cytarabine) as the active ingredient. In particular, the present invention relates to a pharmaceutical composition and the method of preparation thereof, suitable for parenteral administration of therapeutically effective doses of the said derivatives in order to ameliorate compliance in treatment of cancer.

BACKGROUND OF THE INVENTION

Cytarabine, also known as Ara-C or Cytosar, has long been known as a chemotherapeutic agent in the treatment of acute myelogenous leukemia. Cytarabine has the formula:

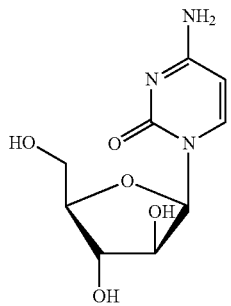

The active ingredients of the pharmaceutical composition of the present invention comprise cytarabine derivatives of the formula I:

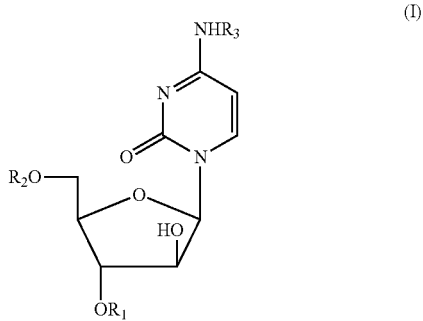

wherein $R_1$, $R_2$ and $R_3$ are independently selected from hydrogen and $C_{18}$- and $C_{20}$-saturated and monounsaturated acyl groups, with the proviso that $R_1$, $R_2$ and $R_3$ cannot all be hydrogen.

Cytarabine has limited efficiency against solid tumors (Frei et al., Cancer Res. 29 (1969), 1325-1332; Davis et al., Oncology, 29 (1974), 190-200; Cullinan et al., Cancer Treat. Rep. 61 (1977), 1725-1726), and even in the treatment of leukemia cytarabine has found only limited use due to its very short biological half-life and its high toxicity.

With a view to overcome these difficulties, a number of workers have prepared and tested pro-drug derivatives of cytarabine. For example, Hamamura et al. investigated 3'-acyl and 3',5'-diacyl derivatives of cytarabine (J. Med. Chem. 19 (1976) No. 5, 667-674). These workers prepared and tested numerous cytarabine derivatives with saturated or unsaturated ester groups containing from 2 to 22 carbon atoms, and they found that many of the compounds showed a higher activity against L1210 Leukemia in mice than the parent nucleoside alone.

Although work has continued on ester pro-drugs based on cytarabine, including 3'- and 5'-acyl derivatives (see, for instance, Rubas et al. in Int. J. Cancer, 37, 1986, pages 149-154 who tested liposomal formulations of 5'-oleyl-cytarabine against L1210 Leukemia and Melanoma B16) to date no such drugs have become available to the clinician.

A main reason why cytarabine is not used in the treatment of solid tumors is the rapid clearance of the active drug from cancer cells and plasma. It is apparently not possible to achieve significant intracellular levels of drug in the neoplastic tissue, even though the tumor in question is sensitive to cytarabine in vitro. We have earlier shown that the derivatives of formula I have prolonged half life and altered tissue distribution which are of great importance for the therapeutic effect of these products (WO 97/05154).

The development of resistant cancer cells is a severe problem in the current chemotherapy of cancer. It was found earlier that one of derivatives of formula I, elacytarabine (5'-O-(trans-9"-octadecenoyl)-1-β-D-arabinofuranosylcytosine), shows the same effect against Cis-platin resistant cells (NHIK 3025/DDP) and MDR resistant cells (A549) as against the corresponding non-resistant cell lines. This is because the ester derivatives are not substrates for the cellular drug-efflux mechanisms, such as the "gp 120 MDR pump", responsible for the phenomenon seen as multi drug resistance.

Nevertheless, formulation of a therapeutically effective amount of the poorly soluble derivatives of formula (I) into a pharmaceutical composition suitable for parenteral administration represents a problem. For the sake of intravenous administration of the said derivatives, the composition of the excipients should be selected so that the said derivatives are solubilised. The cytarabine derivatives of formula (I) are amphiphilic and have poor solubility both in water and in oils. This limits the choice of potential excipients that can solubilise them. As an example, elacytarabine has a solubility of <0.1 μg/ml in deionised water and <1 μg/ml in phosphate buffer pH 7.4 at 25° C. Also, earlier formulation studies showed that elacytarabine did not dissolve appropriately in soybean oil based emulsions, which confirms the low solubility of the drug in oils.

If the formulation is a particulate system, there are certain requirements for the size of the particles in the formulations for intravenous administration. Moreover, parenteral products must be sterile and often sterile filtration is the only viable method for pharmaceutical particulate systems. This means that the particle size of these formulations must be smaller than 220 nm (0.22 μm), which is the pore size of the sterile filters. In practice and for an industrial scale process, the particles should be much smaller to avoid filter clogging.

Another issue is that the daily recommended dose for intravenous elacytarabine when given as a single therapy is recently established at 2000 mg/m². This means that for an average patient with a surface area of 1.8 m², the total daily dose of elacytarabine will be 3600 mg. This introduces even further challenges: a) requirement of increasing the concentration of the drug in the formulation in order to limit the parenteral administration of unacceptably large volumes of liquids to the patients, b) avoiding the use of antioxidants and preservatives, which although added at small amounts, will add up to an unacceptable level of the total administered amount, and c) limiting the quantities of the added surfactants and co-solubilizers due to the same reason as above.

Finally, the ester derivatives of formula (I) are prone to hydrolytic degradation in physiological pH, the rate of which depends on the type of the derivative and the buffer. This represents further challenges both to the formulation and to the manufacturing process parameters. It is normally preferred that a pharmaceutical product be ready-to-use. If ready-to-use, then the said derivatives should be protected from hydrolytic degradation in the aqueous environment of the parenteral formulation during its entire shelf-life period.

The present invention presents a solution to all the above problems.

SUMMARY OF THE PRESENT INVENTION

Figure 1:
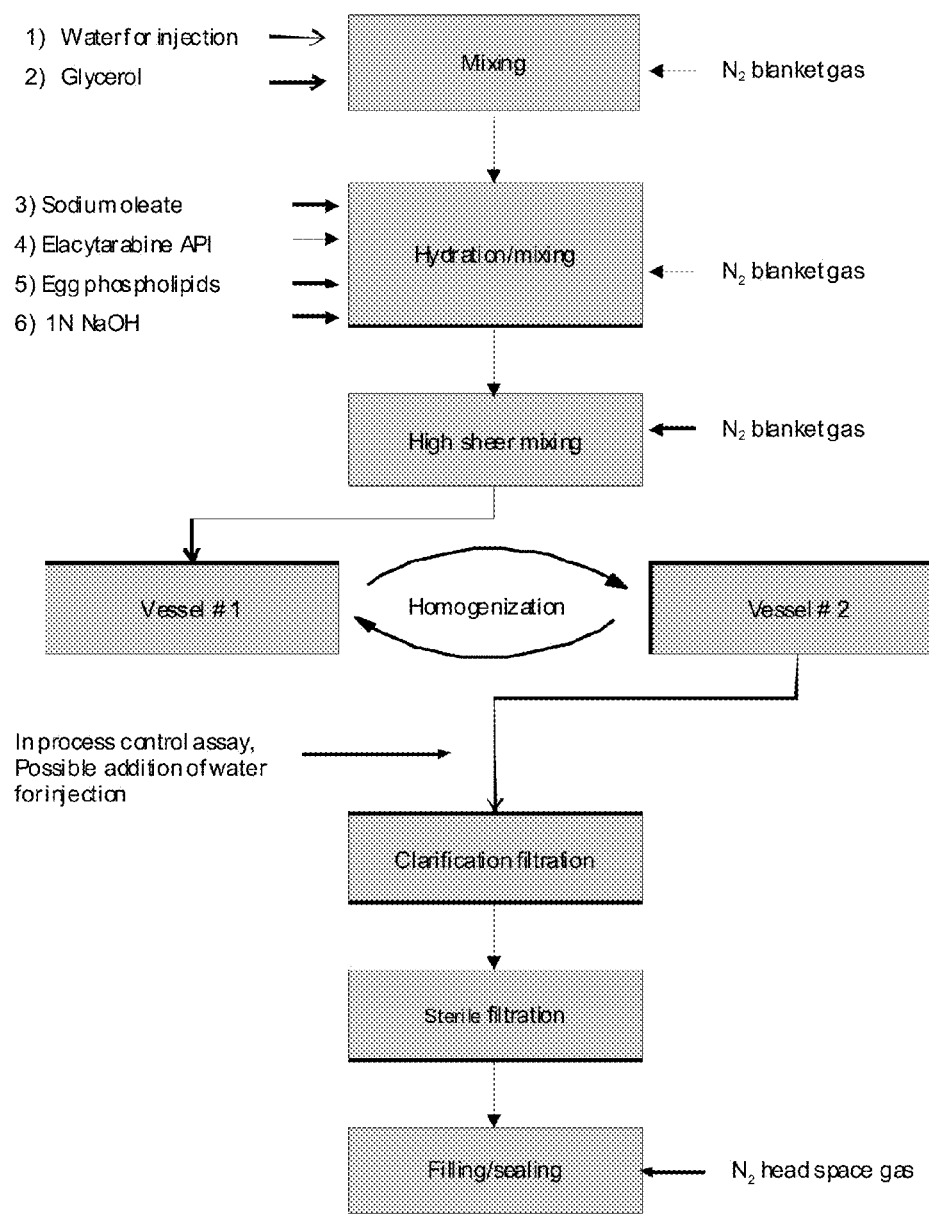
FIG. 1: Elacytarabine Drug Product Process Flow Diagram

It is a main objective of the present invention to provide a pharmaceutical composition suitable for parenteral administration comprising cytarabine derivatives of formula (I) as the active ingredient.

The present invention is further related, in part, to parenteral formulations of elacytarabine (5'-O-(trans-9''-octadecenoyl)-1-β-D-arabinofuranosylcytosine) having the formula:

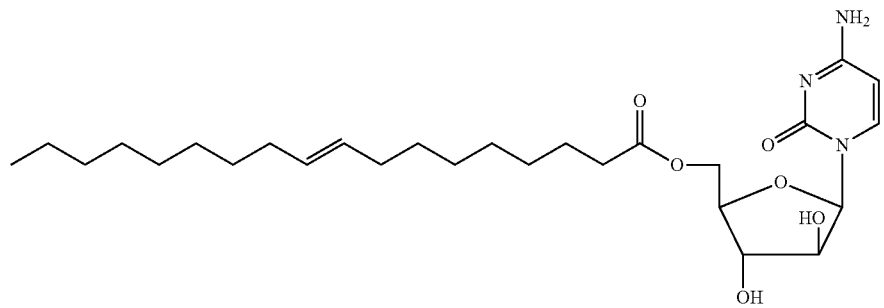

Molecular formula: $C_{27}H_{45}N_3O_6$
Molecular weight: 507.66 g/mol

The present invention is further related, in part, to an elacytarabine formulation comprising: elacytarabine (or salts thereof); a solubilizer comprising one or more phospholipids; a co-solubilizer such as sodium oleate, and an isotonicity agent such as glycerol, in an aqueous medium, preferably at pH 6-8.

The present invention is further related, in part, to a process for preparing elacytarabine lipid based nanoparticulate formulation/liposomes in an aqueous medium.

The present invention is further related, in part, to a method of treating a cell proliferative disorder, comprising administering an elacytarabine lipid based nanoparticulate formulation to a subject in need wherein said subject has a cell proliferative disorder or is at the risk of developing a cell proliferative disorder. It is known from WO 97/05154 that the compounds of formula (I) are useful in treatment of cancer.

We have now surprisingly found a pharmaceutical composition suitable for parenteral administration and a method of preparation for cytarabine derivatives of formula (I) that results in ready-to-use aqueous particulate formulation based on phospholipids, with a drug to lipid molar ratio of between 1:20 and 1:7, preferably between 1:13 and 1:8, where the said lipid particles protect the said derivative from hydrolytic degradation to cytarabine for at least 24 months when stored at 2-8° C. under nitrogen blanket. Furthermore, the method uses natural phospholipids derived from egg yolk and through incorporation of small quantity of a salt of a fatty acid the phospholipids are also protected against hydrolytic degradation. The formed lipid nanoparticles have hydrodynamic diameter of <50 nm, and can be easily sterile-filtered. Additionally, the method of preparation contributes to stabilisation of higher drug loads in the said nanoparticles and is an industrially scalable one, suitable for manufacture of aqueous sterile products.

DETAILED DESCRIPTION OF THE INVENTION

It is a main objective of the present invention to provide a pharmaceutical composition based on natural phospholipids suitable for parenteral administration comprising cytarabine derivatives of formula (I) as the active ingredient, which accommodates therapeutically effective doses of the said derivatives, being as efficacious as, or more efficacious than commercially available cytarabine products, in the treatment of cancer.

This and other objectives of the present invention are achieved by the pharmaceutical composition and method of preparation thereof as described in the attached claims.

Active Pharmaceutical Ingredient

According to an embodiment of the present invention a pharmaceutical composition, comprising a cytarabine derivative of formula I:

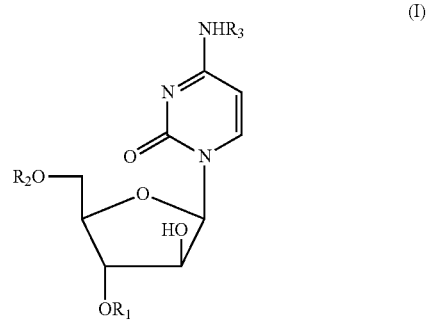

wherein $R_1$, $R_2$ and $R_3$ are independently selected from hydrogen and $C_{18}$- and $C_{20}$-saturated and monounsaturated acyl groups, with the proviso that $R_1$, $R_2$ and $R_3$ cannot all be hydrogen, or a pharmaceutically acceptable salt thereof as the active ingredient; wherein the active ingredient is dissolved or dispersed in phospholipids, is provided.

According to a preferred embodiment of the present invention the phospholipids of the said pharmaceutical composition, comprise a neutrally charged phospholipid alone, or in combination with other phospholipids.

Cytarabine has four derivatisable functions, namely the 5'-, 3'- and 2'-hydroxyl groups and the $N^4$-amino group. The reactivity of the 2'-hydroxyl group is limited in this context and will not be considered. Each group can selectively be transformed into an ester or amide derivative, but di-adducts (di-esters or ester-amides) and tri-adducts may be formed as well. In the case of the di- and tri-adducts the acyl substituent groups need not necessarily be the same.

Currently, the mono-acyl derivatives, i.e. with two of R1, R2 and R3 being hydrogen, are preferred for use as the active ingredient of the present pharmaceutical composition. It is especially preferred that the monosubstitution with the acyl group should be in the 3'-O or 5'-O positions of the sugar moiety, with 5'-O substitution being most preferred.

The double bond of the mono-unsaturated acyl groups may be in either the cis or the trans configuration, although the therapeutic effect may differ depending on which configuration is used.

The position of the double bond in the monounsaturated acyl groups also seems to affect the activity. Currently, we prefer to use esters or amides having their unsaturation in the ω-9 position. In the co-system of nomenclature, the position ω of the double bond of a monounsaturated fatty acid is counted from the terminal methyl group, so that, for example, eicosenoic acid (C20:1 ω-9) has 20 carbon atoms in the chain and a single double bond is formed between carbon 9 and 10 counting from the methyl end of the chain. We prefer to use esters, ester-amides and amides derived from oleic acid (C18:1 ω-9, cis), elaidic acid (C18:1 ω-9, trans), eicosenoic acid(s) (C20:1 ω-9, cis) and (C20:1 ω-9, trans), and the amides and 5'-esters are currently the most preferred derivatives.

Ara-C($N^4$)— elaidic acid amide, Ara-C-5'-elaidic acid ester and Ara-C-3'-elaidic acid ester are among the most preferred derivatives and according to a preferred embodiment of the invention, elacytarabine (Ara-C-5'-elaidic acid ester, or, 5'-O-(trans-9''-octadecenoyl)-1-β-D-arabinofuranosylcytosine) is the active ingredient of the pharmaceutical composition.

The derivatives of formula (I) are prepared according to methods known in the prior art (see WO 97/05154 for further details).

Formulation of the API

The aqueous pharmaceutical composition of the present invention is described below. In general the aqueous formulation requires a solubilizer for the API, a co-solubilizer, an isotonicity agent, and pH control.

According to a preferred embodiment of the invention the pharmaceutical composition comprises elacytarabine, phosphatidylcholine, phosphatidylethanolamine, sphingomyelin, lysophospholipids, natural lipids, fatty acids, sodium oleate, glycerol and water. A particularly preferred formulation is shown below in Table 1.

TABLE 1

Composition of elacytarabine Medicinal Product

| Name of Ingredients | Unit Concentration mg/mL | Function | Reference to Standards |
|---|---|---|---|
| Elacytarabine | 7.5 | Active substance | Clavis Pharma internal |
| Purified egg phospholipids | 100 | Solubilizer | Manufacturer spec. F-K 41 995/01 Fresenius-Kabi |
| Glycerol (anhydrous) | 22.2 | Isotonicity agent | USP/Ph. Eur. |
| NaOH, 1M | 0.75 | To pH approx 7 | National Formulary/ Ph. Eur. |
| Sodium oleate | 1.7 | Co-solubilizer | Manufacturer spec. Sodium Oleate F (Lipoid) |
| Water for injection | To 1.0 ml | Dispersion medium | USP/Ph. Eur. |
| Nitrogen | — | Inert head space gas | National Formulary/ Ph. Eur |

1. Solubilizer

Phospholipids are natural components of cell membranes and are highly biocompatible and we have found them useful in the formulations of elacytarabine described herein. Phospholipids are amphiphilic molecules that spontaneously form bilayers in contact with water and upon further dilution turn into micro- and nanosized vesicular particles called liposomes. Liposomes can encapsulate drug molecules in their aqueous compartment surrounded by the bilayer membrane or intercalate the drug molecule in the bilayer structure. The physicochemical properties of the drug substance is the main factor determining the location of the drug in the liposome particle. Depending on the type of the phospholipids used and the location of the drug, liposomes can perform as two distinctly different delivery systems: 1) an advanced drug delivery system capable of delayed or controlled release, or 2) a solubilizer/stabilizer for the active substance resulting in an immediate release formulation similar to emulsions or suspensions. The latter mechanism is especially relevant in case of lipophilic and amphiphilic molecules, which are basically located in the bilayers of phospholipids and close to the surface of the particles.

Lipophilic or amphiphilic compounds can intercalate in the bilayer structure up to a certain molar ratio without compromising the structure of the liposomes. The maximum drug concentration in such a formulation is dependent on the type and concentration of the phospholipids and the physicochemical characteristics of the active substance. The frequently used molar ratio of the drug to phospholipids in such formulations is in the range of 1:20.

The drug load capacity of such liposomal structures can be positively altered by using an appropriate co-solvent. We have surprisingly found that in the case of formulations of this invention, not only the addition of <2.5% glycerol is enough to stabilize a formulation of the cytarabine derivatives at 8.8 mol % of phospholipids, but also addition of this small amount of glycerol in the right step of the manufacturing process will stabilize the formulation at a higher drug load of 13 mol % relative to the phospholipids. The addition of glycerol at the right step of processing also facilitates the use of lower process temperatures, leading to lower extent of degradation of both the active substance and the phospholipids. Since this small amount of glycerol already creates a marginally hypertonic product, it is essential not to increase the glycerol content and hence the osmolarity even further.

Liposomes are prepared from natural or synthetic phospholipids, mainly phosphatidylcholine, which has a neutral charge in relevant physiologic pH. For the purpose of stabilisation of these colloidal particles, a smaller amount of a negatively charged material may also be incorporated. The electrostatic repulsion due to the negative charge of the particles provides an effective barrier to aggregation and formation of larger particles. The negative charge on the particles can be provided by any negatively charged substance that can be intercalated in the phospholipid-based bilayer structure. However, there is evidence in the literature that addition of a salt of a fatty acid, e.g. sodium oleate, strongly contributes to the stability of the phospholipids by creating a favourable microenvironment (Werling et al., Eur. J. Pharm. Biopharm. 69 (2008) 1104-1113). Hydrolysis kintetics of phosphatidylcholine is pseudo $1^{st}$ order with the minimum rate near pH 6.5 (Grit et al., J. Pharm. Sci. 82 (1993) 362-366). This reaction generates free fatty acids that decreases the bulk pH and increases the magnitude of the negative charge on the surface of the particles. Werling and co-workers (see above reference) suggested that addition of fatty acid anions to a phospholipid based particulate system not only stabilizes the particles through the introduction of a net negative charge, but also influences the surface microenvironment, reduces the hydrolysis kinetics, and contributes to overall enhancement of the suspension physicochemical stability. However, they used a 1:4 molar ratio of sodium oleate to egg phospholipids, while in our formulations a molar ratio of 1:23 is unexpectedly resulting in similar benefit.

Elacytarabine is an amphiphilic compound which in aqueous media may be solubilized by association with the bilayers formed by purified egg phospholipids. Purified egg phospholipids are a mixture of compounds. The major (ca 90%) phospholipid constituents of purified egg phospholipids are shown in Table 2. Further, a typical fatty acid profile, relative amount and position in the molecule of egg phosphatidylcholine (PC) is shown in Table 3. All the phospholipid constituents are amphiphilic compounds with some resemblance to elacytarabine (polar head-lipophilic tail). These amphiphilic features are utilized in the formulation of elacytarabine.

TABLE 2

Major constituents of purified egg phospholipids

| Phospholipid | Abbreviations | Mw | Chemical structure |
|---|---|---|---|
| Phosphatidylcholine | PC | 770 | (structure) |
| Lyso-phosphatidyl-chlolines (1 & 2) | 1-LPC & 2-LPC | 515 | (structure) |
| Phosphatidylinositol | PI | 835 | (structure) |
| Sphingomyelin | SPH | 770 | (structure) |
| Phosphatidyl-ethanolamine | PE | 725 | (structure) |
| Lyso-phosphatidyl-ethanolamine | LPE | 470 | (structure) |

TABLE 3

Position of different fatty acids in the PC fraction of egg phospholipids

| Fatty acid* | % in position 1 in glycerol backbone | % in position 2 in glycerol backbone |
|---|---|---|
| 16:0 | 68.8 | 1.8 |
| 18:0 | 25.8 | 3.2 |
| 18:1 | 4.7 | 48.9 |
| 18:2 | 0.2 | 13.1 |
| 18:3 | 0.5 | |
| 20:4 | | 2.1 |
| 20:5 | | 7.1 |

TABLE 3-continued

Position of different fatty acids in the PC fraction of egg phospholipids

| Fatty acid* | % in position 1 in glycerol backbone | % in position 2 in glycerol backbone |
|---|---|---|
| 22:5 | | 2.6 |
| 22:6 | | 25.2 |
| Total | 100 | 100 |

*No of carbon atoms, No of double bonds

The concentration of the purified egg phospholipids has been optimized to incorporate the target amount of the drug substance in the phospholipid bilayers. The average molecular weight for the phospholipid fraction of purified egg phospholipids is 764 g/mol. The lipid content is ca 91±1% w/w. Based on this, the addition of 100 mg/mL purified egg phospholipids to the formulation as shown in Table 1 equals a lipid content of ca 91±1 mg/mL. Accordingly, with a lipid and API concentration of 91 mg/mL and 7.5 mg/mL respectively, the molar ratio between the lipids and the API in the elacytarabine formulation is ca 8:1.

The lipid particles of the formulation may comprise, but are not restricted to, the following phospholipids, which function as solubilizers, bilayer-forming or micelle-forming excipients: phosphatidylcholine, phosphatidylethanolamine, sphingomyelin, lysophospholipids, phosphatidylinositol, phosphatidylserine, phosphatidylglycerol, phosphatidic acid, cardiolipin. The phospholipids may be in any form, including salted or desalted, hydrogenated or partially hydrogenated, natural, semisynthetic or synthetic. Also, attachment of hydrophilic polymers such as polyethyleneglycol (PEG) to the phospholipids in order to avoid rapid clearance by the reticuloendothelial system (RES) is possible.

In a preferred embodiment natural unsaturated phospholipids derived from hen egg are used alone or in combination.

In still another embodiment of the invention the natural egg phospholipids comprise a zwitterionic phospholipid which is neutral in the pH range of 6-8 such as egg phosphatidylcholine.

2. Co-Solubilizer

In one embodiment, a co-solubilizer is added. In a preferred embodiment, this co-solubilizer is selected from the group of surfactants. In a more preferred embodiment, this co-solubilizer also has a function of stabilizer through introduction of a negative charge. In a still more preferred embodiment, an anionic surfactant such as a salt of a fatty acid is selected. In yet more preferred embodiment this co-solubilizer also protects the phospholipids from hydrolytic degradation. In the most preferred embodiment, this co-solubilizer is sodium oleate.

3. Isotonicity Agent

In one embodiment of the invention, an isotonicity agent is included in the pharmaceutical composition. In a more preferred embodiment, this isotonicity agent is selected from the following list: glycerol, propyleneglycol, sugar, aminoacids or proteins, salts, and a mixture thereof.

In the most preferred embodiment, this isotonicity agent is glycerol. Glycerol as a co-solvent is added to facilitate the dispersion of elacytarabine particles and the incorporation of the drug in the lipid nanoparticles. The amount added is between 0.1% and 30% w/v of the final pharmaceutical composition, more preferably 1-10% w/v and most preferably 2-5% w/v of the final pharmaceutical composition.

The amount of isotonicity agent may vary between 1 to 50% of the final pharmaceutical composition, more preferably 5 to 15% and most preferably 7-10%. All subranges between 1 and 50% are included as part of the invention.

In another embodiment, the molar ratio of the isotonic agent to total phospholipids is between 10:1 and 1:5, more preferably 5:1 to 1:1. All subranges between 10:1 and 1:5 are included as part of invention.

4. pH Control

In yet another embodiment, a base is added to adjust the pH and to strengthen the negative charge of the particles. A base, as used herein, includes a chemical compound that accepts protons. An example of a base includes, but is not limited to, a metal hydroxide (e.g., lithium hydroxide, sodium hydroxide, potassium hydroxide, magnesium hydroxide, calcium hydroxide, barium hydroxide, and strontium hydroxide), a carbonate base (e.g., lithium carbonate, sodium carbonate, potassium carbonate, magnesium carbonate, calcium carbonate, strontium carbonate and lanthanum carbonate), an amine base (e.g., ammonia), and a mixture thereof.

In a preferred embodiment, this base is sodium hydroxide. Sodium hydroxide may be added, e.g. as a 0.1-10M solution. The amount is adjusted to result in a pH of approximately 7 in the final pharmaceutical composition. All ranges of concentrations resulting in a final pH of 6-8 is included as a part of the invention.

5. Manufacture of the Formulation

The present invention also provides a process for the preparation of a pharmaceutical composition as mentioned above.

In one preferred embodiment of the invention, the composition of the excipients, the drug to lipid ratio and the method for manufacture is selected to favour a liposomal bilayer structure. In another embodiment, the said parameters are selected to favour micellar nanoparticles, or a combination of micelles and liposomes.

In one embodiment, the water dispersable ingredients, e.g. glycerol and sodium oleate, are added to heated water, followed by sodium hydroxide and the phospholipids. The derivative of formula (I) is added and dispersed using high shear mixer until solibilized. The bulk product is then homogenised in several cycles until final particle size is achieved, followed by sterile filtration and aseptic filling. In a more preferred embodiment, glycerol is added to heated water and the derivative of formula (I) is dispersed in this mixture using high-shear mixer. The rest of the excipients are added and mixed, before the bulk product is homogenised and sterile-filtered as mentioned above.

The flow diagram for a preferred manufacture process is shown in FIG. 1. Specifically, in the first step water for injection is mixed with glycerol and heated to the target temperature of 45° C. In the second manufacturing step, sodium oleate, elacytarabine API, egg phospholipids and NaOH is added stepwise with subsequent stirring maintaining a temperature of 45° C. In the third step the bulk product is mixed with a rotor stator mixer at 45° C. for one hour. In the fourth step the product is homogenized at 25000 psi for not less than three cycles to obtain a satisfactory particle size. As an in process control, the mean particle size, particle size distribution profile and the turbidity is measured after each homogenization cycle. If the turbidity is less than 600 NTU after homogenization cycle number 3, it is prepared for the next process step. If the turbidity is higher than 600 NTU, another homogenization cycle is performed. Upon compliant turbidity, the assay is measured. If the assay value is <102.0%, no correction is performed. If the value is ≥102.0%, a calculated amount of water for injection is added to target an assay value of 100%. The pH is measured for information only. In the fifth step, a clarification filtration is performed by serial filtration of the solution through 1.2 µm and 0.45 µm filters. Next, the bulk product is sterile filtered through two sterile 0.22 µm filters. The filters are checked for integrity and bubble point using water for injection before they are steam sterilized. The first filter, which is in direct contact with the non-sterile bulk, is tested for integrity using the bulk product just before sterile filtration. Both filters are tested for integrity and bubble-point post-filtration. In the last process step, the sterile filtered product is aseptically filled into sterilized, depyrogenated glass bottles in a continuous manner. The filled bottles are purged with nitrogen and immediately sealed with sterile rubber stoppers and aluminum caps.

The particles of the final pharmaceutical composition are either liposome-like, meaning vesicles surrounded by phospholipid bilayer, or micelle-like, or a combination of both. The particle size of the final pharmaceutical composition may be in the range of 5-45 nm, preferably 9-25 nm, most preferably in the range 10-20 nm with a mean particle size of about 15 nm.

The pharmaceutical composition according to the invention is preferably in liquid form, and may be presented in discrete units such as vials, infusion bags or the like. The pharmaceutical form of the final composition is a suspension or dispersion, either liposomes or micelle-like nanoparticles, or a combination of both.

The amount of the phospholipid phase in the final pharmaceutical composition may vary from about 0.1% to 50%, preferably 1-15%, and more preferably 5-12%. In the most preferred but not limiting embodiment, the amount of the phospholipid phase is 8-10% of the final pharmaceutical composition. All subranges from 0.1% to 50% are included as part of the invention.

The molar ratio of the elacytarabine derivative of formula (I) to the total amount of the phospholipids in the final pharmaceutical composition may vary from 1:20 to 1:7. The most preferable range is 1:13 to 1:8. All subranges between 1:20 and 1:7 are included as part of the invention. In a preferred embodiment the final formulation contains between 5.0 mg/ml and 7.5 mg/ml elacytarabine, most preferably 7.5 mg/ml elacytarabine.

The molar ratio of egg phosphatidylcholine to egg phosphatidylethanolamine in the composition may vary from 1:1 to 99:1, preferably 2:1 to 80:1, with the most preferable ratio being in the range of 4:1 and 10:1. All subranges between 1:1 and 99:1 are included as a part of the invention.

6. Dosing

The term "therapeutically effective amount" as used herein refers to from about 0.001 to 10 grams per day of a cytarabine derivative of formula (I) or a pharmaceutically acceptable salt thereof, more preferred from about 10 mg to 6 grams per day of a cytarabine derivative of formula (I) or a pharmaceutically acceptable salt thereof, in a formulation containing 0.001-80% of the said derivative or salt thereof formulated for parenteral administration.

The pharmaceutical compositions of this invention are useful in treating a wide variety of cancers.

For solid tumor cancers, such as ovarian cancer, non-small cell lung cancer, colorectal cancer and malignant melanoma, the preferred dosing schedule for intravenous elacytarabine is 200 mg/m$^2$ once daily for 5 days, with a 2-3 week rest period between courses of administration.

For hematologic cancers, such as leukemias, and specifically including acute myeloid leukemia, preferably the daily recommended dose for intravenous elacytarabine when given as a single therapy or monotherapy is 2000 mg/m$^2$. This means that for an average patient with a surface area of 1.8 m$^2$, the total daily dose of elacytarabine will be 3600 mg. In this embodiment, the preferred dosing schedule for intravenous elacytarabine formulations of this invention is 2000 mg/m$^2$ continuous infusion over 5 days, with a 2-3 week rest period between courses of administration.

For hematologic cancers, such as leukemias, and specifically including acute myeloid leukemia, preferably the daily recommended dose for intravenous elacytarabine when given as a combination therapy (such as with idarubicin) is 1000 mg/m$^2$. This means that for an average patient with a surface area of 1.8 m$^2$, the total daily dose of elacytarabine will be 1800 mg. In this embodiment, the preferred dosing schedule for intravenous elacytarabine formulations of this invention is 1000 mg/m$^2$ continuous infusion over 5 days, with a 2-3 week rest period between courses of administration.

In the following the invention will be further explained by examples. The examples are only meant to be illustrative and shall not be considered as limiting.

EXAMPLES

Example 1

Glycerol (2.22%) and sodium oleate (0.17%) were added to water at 75° C. and stirred. A 1M solution of sodium hydroxide was added to achieve a pH value of 7-8.10% purified egg phospholipids (PL90, Fresenius-Kabi) was added and dispersed by high-shear stirrer. Elacytarabine (0.5%) was added and stirred. The product was homogenised at 50° C. in several cycles until satisfactory particle size was achieved. Thereafter, the product was sterile filtered, filled in glass vials, and sealed under nitrogen blanket.

The vials were stored at 2-8° C. protected from light, and the stability of the batch was monitored up to 24 months. During the course of this stability study, less than 2.5% decrease in the content of elacytarabine was observed.

Example 2

A glycerol solution of 2.22% w/w in water was prepared and heated to 50° C. Elacytarabine was added to 0.75% w/v concentration under vigorous high-shear stirring until finely dispersed. Sodium oleate, sodium hydroxide and egg phospholipids were added in the same concentrations as in example 1, one at a time and mixed thoroughly. The bulk product was homogenised at 50° C. in several cycles until satisfactory particle size was achieved, sterile filtered, filled in glass vials, and sealed under nitrogen blanket.

In a separate experiment, elacytarabine was formulated at 7.5 mg/ml according to the process in Table 4 below:

TABLE 4

Elacytarabine Drug Product process and manufacturing details

| Process step | Material name/amount | Time/temp/stirring rate | IP check and control | Comments |
|---|---|---|---|---|
| Step 1 Mixing and heating of water and glycerol | Water; 90 kg (70%) Glycerol; 3.330 kg | Mixing at 45 ± 3° C. for 10 ± 2 min at 300 to 500 RPM (target 300 RPM) with propeller mixer. | Check temperature Check stirring speed | |

TABLE 4-continued

Elacytarabine Drug Product process and manufacturing details

| Process step | Material name/amount | Time/temp/stirring rate | IP check and control | Comments |
| --- | --- | --- | --- | --- |
| Step 2 Hydration and mixing | Sodium oleate; 255 g API; 1125 g Egg phospholipids; 15.0 kg 1N NaOH; 112.5 g Water to QS | Temperature 48 ± 3° C. Propeller mixer target 300 RPM and high sheer mixer target 57 Hz for 7 ± 2 min after addition of each starting material. | Visual inspection to verify dispersion. Weight check | No visible lumps. |
| Step 3 High sheer mixing | Water to QS | Temperature 48 ± 3° C. High sheer mixer at 57 Hz for 60 ± 5 min Propeller mixer target 400 RPM for 5 ± 2 min after addition of water | Check pH after end of mixing. Weight check | Add water after end of high sheer mixing to compensate for any evaporation |
| Step 4 Homogenization | Water to correct for assay | Pressure 25000 ± 1000 psi Bulk temperature 48 ± 3° C. Propeller mixer in reservoir and receiver vessels target 400 RPM | Determine mean particle size and particle size distribution and turbidity per pass. Check pH after end of homogenization. Check if assay value ≤ 102.0% < Weight check | If turbidity < 600 NTU after pass 3, prepare for step 5. If assay ≥ 102.0% add water to QS 100%. If assay < 102.0%, prepare for step 5 Cool bulk solution while awaiting assay results |
| Step 5 Clarification filtration | | Bulk temperature 23 ± 2° C. | Sample for bacterial count. | |
| Step 6 Sterile filtration | | Bulk temperature 23 ± 2° C. | Filter integrity verified pre and post filtration | Filter ca 80 Liter to filling carboy before step 7 starts |
| Step 7 Filling and sealing | | Ambient room temperature in filling suite | | |

Example 3

Degree of Oxidation and Hydrolysis of Phospholipids

Formulations of example 1 were tested for degree of oxidation and hydrolysis of phospholipids.

In order to avoid oxidation of the fatty acids, the drug product is manufactured under low oxygen nitrogen blanket and the vials are purged with nitrogen before being sealed.

We performed an experiment to determine and compare the degree of oxidation of the fatty acids in 2 selected batches of drug product, one batch was 16 months old from production, the other was 3 months old from production upon start of the analytical program. The experiments on the named batches were performed in parallel, meaning that one "fresh" and one "older" batch were compared in all the experiments. Both were tested on peroxide value, anisidine value, phospholipid profile and total content by $^{31}$P-NMR, UV analysis for the ratio of conjugated dienes and trienes, oxygen content and malondialdehyde assay for measurement of cyclic peroxides.

The results confirmed that the degree of oxidation of the phospholipids is negligible.

The batches were also stressed under oxygen blanket and 40° C., where it was possible to promote and measure the oxidation. In addition, placebo batches have been prepared and subsequently been oxygen-stressed to confirm the above observations also in the absence of the drug substance.

The results of these extensive studies provide enough assurance that nitrogen blanketing and storage at 2-8° C. of the drug product are effective oxidation-preventive actions.

Another important degradation pathway for phospholipids is hydrolysis. The amount of lysophosphatidylcholine has been monitored throughout the stability studies of the product. It was shown that in total less than 3.5 mol % of phosphatidylcholine was hydrolyzed to the lyso-products in the course of the manufacturing process and the 24 months storage at 2-8° C. This confirms the protective effect of sodium oleate on the phospholipids.

Example 4

Thermal analysis by Differential Scanning calorimetry (DSC) of the formulation described in example 1 was performed to confirm the storage and shipment temperature of the product. It was shown that the freezing point was low at −19.3° C., probably due to supercooling of water. The melting point was at approximately −3.5° C. This suggested that a storage and shipment temperature of 2-8° C. would not cause melting or freezing of the phospholipids and hence would not pose any negative impact on the structure of the particles.

Example 5

The formulation described in example 1 was administered to 61 patients in a phase II study of single agent elacytarabine as second salvage therapy for acute myeloid leukemia (AML). The study data showed statistically significant superior efficacy in refractory/relapsed patients with very poor disease prognosis. The response rate was 15%. The median overall survival was 5.3 months versus 1.5 months in the historical control. The median survival for the responders was 13.5 months. The 6 month survival rate was 44%.

Side effects of elacytarabine were predictable and manageable. The product was well tolerated, also by elderly patients.

Figure 2:
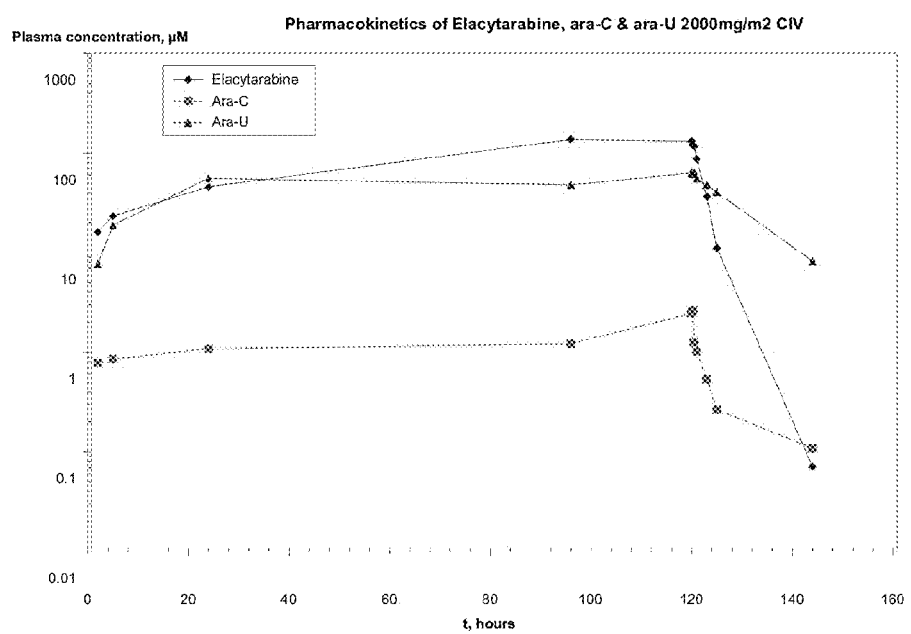
FIG. 2: Plasma concentration of elacytarabine, Ara-C and Ara-U (deamination metabolite of Ara-C), average values for 61 patients.

The pharmacokinetics data presented in FIG. 2 shows at least a 10 fold exposure to elacytarabine compared to cytarabine (Ara-C).

Example 6

We made several attempts to increase the drug to phospholipids ratio in the intravenous formulation of elacytarabine.

The first elacytarabine formulation used in clinical trials was a 10 mg/ml, with the exact same composition as described in example 1, only lager amount of elacytarabine. This product precipitated several months after the manufacture and was withdrawn from the clinical sites. The subsequent analysis of the supernatant showed that the remaining drug in the liposomes was 7-7.5 mg/ml.

Another series of formulations were done to examine the effect of other phospholipid combinations and changing the method of preparation to a solvent injection one. The first series of experiments are summarised in Table 5. The process consisted of dissolving the phospholipids and elacytarabine in ethanol, followed by controlled injection of the said ethanol solution into a glycerol/water solution. The resulting bulk product was homogenised up to 7 cycles and then concentrated to the target volume by Tangential Flow Filtration (TFF) and the excess ethanol was removed by the same method.

TABLE 5

| | Elacytarabine concentration | | | |
|---|---|---|---|---|
| Lipids | 30 mg/ml | 20 mg/ml | 15 mg/ml | 10 mg/ml |
| Egg phospholipids/ sodium oleate | Precipitation under preparation | Sterile filter block, final content 11.3 mg/ml | Sterile filter block, final content 14 mg/ml | Difficult/impossible to sterile filter, many small particles and crystals observed under microscope, final content 7.7 mg/ml |
| Egg PC/egg PG | Precipitation under preparation | Precipitation during homogenisation | OK, final content 12 mg/ml, slight precipitation upon storage at 2-8° C. | OK, final content 8 mg/ml, large lipid agglomerates seen after filtration, particle size (z-avg) 97 nm |
| Egg PC/egg PG/ Egg PE | — | — | Preipitation upon storage at 2-8° C. | OK, final content 7.4 mg/ml, large lipid agglomerates seen after filtration, particle size (z-avg) 118 nm |

The egg PC/egg PG formulation was further investigated using lower concentrations of the drug: 10, 8.5 and 7.5 mg/ml. The result was respectively 6.5, 6.8 and 5.7 mg/ml content. Further investigations showed that the drug to lipid ratio decreased dramatically during the TFF filtration. More importantly, the ethanol injection method didn't seems to result in higher drug to lipid ratio or any other favourable effect on the formulation compared to the significantly less resource demanding original manufacturing method.

The invention claimed is:

1. A pharmaceutical composition, comprising a cytarabine derivative of formula I:

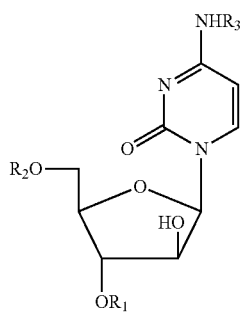

(I)

wherein $R_1$ and $R_3$ are hydrogen and $R_2$ is a $C_{18}$- or $C_{20}$-saturated or monounsaturated acyl group, or a pharmaceutically acceptable salt thereof as an active ingredient;
wherein the active ingredient is dissolved or dispersed in a formulation comprising:
a solubilizer comprising one or more phospholipids,
a co-solubilizer comprising a surfactant, and
an isotonicity agent selected from the group consisting of glycerol, propylene glycol, sugars, amino acids, proteins, salts and combinations thereof,
wherein the formulation has a particle size between 5 nm and 45 nm.

2. The pharmaceutical composition of claim 1, wherein the active ingredient is Ara-C-5'-elaidic acid ester.

3. The pharmaceutical composition according to claim 1, wherein the solubilizer comprises one or more phospholipids selected from the group consisting of phosphatidylcholine, lyso-phosphatidylcholine 1, lyso-phosphatidylcholine 2 phosphatidylglycerol, phosphatidylethanolamine, lyso-phosphatidylethanolamine, phosphatidylinositol, phosphatidylserine, phosphatidic acid, sphingomyelin and cardiolipin, and the salts, desalts, hydrogenates and partial hydrogenates of any thereof.

4. The pharmaceutical composition according to claim 1, wherein the phospholipids are natural unsaturated phospholipids derived from hen egg.

5. The pharmaceutical composition of claim 1, wherein the co-solubilizer is sodium oleate.

6. The pharmaceutical composition according to claim 1, wherein the isotonocity agent is glycerol.

7. The pharmaceutical composition according to claim 1, wherein the pH of the formulation is between 6.0 and 8.0.

8. The pharmaceutical composition according to claim 1, wherein the particle size is between 9-25 nm.

9. The pharmaceutical composition according to claim 1, wherein the formulation has a drug:lipid molar ratio of between 1:20 and 1:7.

10. The pharmaceutical composition according to claim 1, wherein the formulation has a drug:lipid molar ratio of between 1:13 and 1:8.

11. The pharmaceutical composition according to claim 1, wherein the formulation has a final elacytarabine concentration of between 5.0 and 7.5 mg/ml.

12. A method of preparing the pharmaceutical composition of claim 1, comprising the steps of:

a) mixing water and the isotonicity agent and heating the mixture;
b) adding the solubilizer, co-solubilizer, and the active ingredient to the mixture of step a) and mixing with high shear;
c) homogenizing the mixture of step b) by exposing the mixture to high pressure, and
d) filtering the resultant product.

13. The method of claim 12, wherein the mixture of step a) is heated at 45° C.±5° C.

14. The method of claim 12, wherein the mixing at high shear in step b) is perfomed at about 57 Hz for about one hour.

15. The method of claim 12, wherein the homogenizing at high pressure in step c) is perfomed at about 25000 psi.

16. A method of treatment of solid tumors, wherein said method of treatment comprises administering to a patient in need thereof the pharmaceutical composition of claim 1 at a dose of 200 mg/m$^2$ once daily for 5 days, with a 2-3 week rest period between courses of administration.

17. A method of treatment of hematologic tumors, wherein said method of treatment comprises administering to a patient in need thereof the pharmaceutical composition of claim 1 as a monotherapy at a dose of 2000 mg/m$^2$ once daily for 5 days, with a 2-3 week rest period between courses of administration.

18. A method of treatment of hematologic tumors, wherein said method of treatment comprises administering to a patient in need thereof the pharmaceutical composition of claim 1 as a combination therapy at a dose of 1000 mg/m$^2$ once daily for 5 days, with a 2-3 week rest period between courses of administration.

* * * * *